United States Patent [19]
Ebert et al.

[11] Patent Number: 5,302,395
[45] Date of Patent: Apr. 12, 1994

[54] METHOD AND SYSTEMS FOR ADMINISTERING NITROGLYCERIN TRANSDERMALLY AT ENHANCED TRANSDERMAL FLUXES

[75] Inventors: Charles D. Ebert, Salt Lake City; Dinesh Patel, Murray; Sonia Heiber, Salt Lake City, all of Utah

[73] Assignee: TheraTech, Inc., Salt Lake City, Utah

[21] Appl. No.: 919,296

[22] Filed: Jul. 24, 1992

Related U.S. Application Data

[62] Division of Ser. No. 625,906, Dec. 10, 1990, Pat. No. 5,202,125.

[51] Int. Cl.⁵ .............................................. A61F 13/00
[52] U.S. Cl. .................................... 424/449; 424/443; 424/447; 424/448; 514/946; 514/947
[58] Field of Search ............... 424/449, 448, 447, 443; 514/946, 947

[56] References Cited

U.S. PATENT DOCUMENTS

| | | | |
|---|---|---|---|
| 4,482,534 | 11/1984 | Blank | 424/486 |
| 4,559,222 | 12/1985 | Enscore et al. | 424/449 |
| 4,615,699 | 10/1986 | Gale et al. | 424/449 |
| 4,685,911 | 8/1987 | Konno et al. | 424/449 |
| 4,690,683 | 9/1987 | Chien et al. | 424/448 |
| 4,698,062 | 10/1987 | Gale et al. | 424/449 |
| 4,751,087 | 6/1988 | Wick | 424/449 |
| 4,764,381 | 8/1988 | Bodor et al. | 424/449 |
| 4,764,382 | 8/1988 | Kydonieus et al. | 424/449 |
| 4,792,450 | 12/1988 | Kydonieus et al. | 424/419 |
| 4,814,168 | 3/1989 | Sablotsky et al. | 424/78 |
| 4,836,970 | 9/1989 | Patel et al. | 514/772 |
| 4,879,119 | 11/1989 | Konno et al. | 424/449 |

FOREIGN PATENT DOCUMENTS

| | | |
|---|---|---|
| 0152281 | 8/1985 | European Pat. Off. |
| 0328806 | 8/1989 | European Pat. Off. |
| 0413034 | 2/1991 | European Pat. Off. |
| WO83/00093 | 1/1983 | PCT Int'l Appl. |
| WO86/00814 | 2/1986 | PCT Int'l Appl. |
| WO90/11065 | 10/1990 | PCT Int'l Appl. |

OTHER PUBLICATIONS

Ogiso et al., *J. Pharmacobio-Dyn.* (1986) 9:517-525.
Ogiso et al., *J. Pharm. Sci.* (1989) 78(4):319-323.
Shen et al., *J. Pharm. Sci.* (1976) 65(12):1780-1783.
Aungst et al., "Enhancement of naloxone penetration through human skin using fatty acids, fatty alcohols, surfactants, sulfoxides, and amines" *International Journal of Pharmaceutics* (1986) 33(1-3):225-234.

*Primary Examiner*—Thurman K. Page
*Assistant Examiner*—D. Gabrille Phelan
*Attorney, Agent, or Firm*—Morrison & Foerster

[57] ABSTRACT

Transdermal delivery systems for delivery of nitroglycerin are disclosed which deliver the drug at enhanced transdermal fluxes. The systems include, in addition to nitroglycerin, a permeation enhancer which is either a sorbitan ester, a $C_8-C_{22}$ aliphatic alcohol, or a mixture thereof. Methods for administering nitroglycerin using such permeation enhancers are also disclosed.

14 Claims, 1 Drawing Sheet

METHOD AND SYSTEMS FOR ADMINISTERING NITROGLYCERIN TRANSDERMALLY AT ENHANCED TRANSDERMAL FLUXES

This application is a division of application Ser. No. 07/625,906 filed, Dec. 10, 1990, now U.S. Pat. No. 5,202,125.

TECHNICAL FIELD

The present invention relates generally to the transdermal administration of nitroglycerin, and more particularly relates to novel methods and systems for transdermally administering nitroglycerin at enhanced transdermal fluxes.

1. Background

Nitroglycerin is a drug that has been administered as a prompt-acting vasodilator in the relief and treatment of angina pectoris. Nitroglycerin has also been used at somewhat higher doses in the treatment of congestive heart failure. The principal pharmacological action of nitroglycerin is relaxation of vascular smooth muscle, so as to produce a vasodilator effect on both peripheral arteries and veins.

Nitroglycerin was originally administered orally and, later, bucally. More recently, transdermal systems have been developed which have been found to improve the systemic bioavailability of the drug. The Nitro-Dur® Transdermal Infusion System manufactured and sold by Key Pharmaceuticals, Inc. (Kenilworth, N.J.) the Nitrodisc® made by Searle Pharmaceuticals, Inc. (Chicago, Ill.), the Nitroglycerin Transdermal System of Bolar Pharmaceutical Co., Inc. (Copiague, N.Y.), the Transderm-Nitro® system distributed by CIBA Pharmaceutical Co. (Summit, N.J.), and the Minitran® system of Riker Pharmaceuticals (St. Paul, Minn.) are examples of the currently available transdermal nitroglycerin systems.

Several problems which have been encountered with the transdermal administration of nitroglycerin include the tolerance to the drug which results from prolonged administration. Higher and higher doses are required for patients on long-term nitroglycerin therapy, necessitating the use of larger and larger transdermal patches. This is obviously inconvenient and undesirable. Accordingly, the present invention is directed to a method and system for administering nitroglycerin transdermally, and provides for a relatively high transdermal flux using a more conveniently sized, smaller patch. The invention may also be useful to treat indications other than angina pectoris, e.g., congestive heart failure or production of controlled hypotension during surgery and perioperative to surgery, which require higher doses of nitroglycerin. The invention involves the transdermal administration of nitroglycerin in combination with a low irritation skin permeation enhancer—either a sorbitan ester, a $C_8$–$C_{22}$ aliphatic alcohol, or a mixture thereof.

2. Citation of Art

The following references relate to one or more aspects of the present invention.

Transdermal administration of nitroglycerin, generally: U.S. Pat. No. 4,751,087 to Wick describes an acrylate-based adhesive tape for delivering nitroglycerin transdermally. The system optionally includes as a skin penetration enhancing combination (i) a fatty acid ester, and (ii) glyceryl monolaurate. U.S. Pat. No. 4,615,699 to Gale et al. describes a transdermal delivery system for administering nitroglycerin in conjunction with ethanol as a skin permeation enhancer. U.S. Pat. No. 4,764,381 to Bodor et al. describes nitroglycerin compositions for transdermal administration, containing oleic acid as a permeation enhancer. U.S. Pat. No. 4,559,222 to Enscore describes a matrix composition for transdermal drug administration, the matrix containing mineral oil, polyisobutylene, and colloidal silicon dioxide U.S. Pat. No. 4,698,062 to Gale et al. relates to a transdermal drug delivery device which effects "pulsatile" delivery of nitroglycerin to a patient. U.S. Pat. No. 4,814,168 to Sablotsky et al. describes transdermal drug delivery systems stated to be useful in the administration of nitroglycerin, the systems containing a "multipolymer" drug reservoir of vinyl acetate, polyethylene, rubber, and a tackifying agent. PCT Publication No. W083/00093, inventors Keith et al., relates to a polymeric diffusion matrix for the transdermal administration of nitroglycerin which contains two polyvinyl alcohol components and glycerol. PCT Publication No. W086/00814, inventors Sablotsky et al., relates to an adhesive bilayer transdermal delivery system for the administration of nitroglycerin.

Permeation enhancers: T. Ogiso et al., *J. Pharmacobio-Dyn.* 9:517–525 (1986) presents studies on percutaneous absorption in vivo and the penetration in vitro of indomethacin. Sorbitan monooleate was tested as a permeation enhancer in combination with a dimethyl sulfoxide (DMSO) gel and was found to have no enhancing effect. T. Ogiso et al., *J. Pharm. Sci.* 78(4):319–323 (1989) describes the combined use of laurocapram (Azone®) and sorbitan monooleate in a permeation enhancer composition also containing a DMSO gel, for the transdermal administration of indomethacin. W.-W. Shen et al., *J. Pharm. Sci.* 65(12):1780–1783 (1976) describes the effect of various nonionic surfactants, including sorbitan monopalmitate and sorbitan trioleate, on the percutaneous absorption of salicylic acid. As with the latter two references, the sorbitan esters are used in conjunction with DMSO.

SUMMARY OF THE INVENTION

Accordingly, it is a primary object of the invention to address the above-mentioned needs in the art, and to provide a method for administering nitroglycerin transdermally at a relatively high transdermal flux, in turn enabling the use of a convenient, smaller-sized transdermal patch.

It is another object of the invention to provide such a method for administering nitroglycerin transdermally which involves administration of the drug in combination with a low irritation skin permeation enhancer.

It is still another object of the invention to provide a method for administering nitroglycerin transdermally involving administration of the drug with a skin permeation enhancer which is either a sorbitan ester as will be defined herein, a $C_8$–$C_{22}$ aliphatic alcohol as will be defined herein, or a mixture thereof.

It is a further object of the invention to provide such a method in which the nitroglycerin and the skin permeation enhancer are administered simultaneously using a laminated composite as a transdermal patch which contains drug and the selected permeation enhancer in one or more drug reservoir layers.

It is still a further object of the invention to provide a transdermal system for the administration of nitroglycerin which provides for a drug flux of at least about 50% higher than that obtained in the absence of a skin permeation enhancer.

Additional objects, advantages and novel features of the invention will be set forth in part in the description which follows, and in part will become apparent to those skilled in the art upon examination of the following, or may be learned by practice of the invention.

In one aspect, the invention is a method for administering nitroglycerin transdermally so as to achieve relatively high transdermal fluxes, by coadministering, through a predetermined area of intact skin and for a predetermined period of time, (1) nitroglycerin, and (2) a permeation enhancer selected from the group consisting of (a) sorbitan esters, (b) $C_8$-$C_{22}$ aliphatic alcohols, and (c) mixtures thereof. In a preferred embodiment, the skin permeation enhancer and the drug are administered in a single composition which contains both components. As the clearance rate of nitroglycerin from the body is quite high, it is preferred that administration be continuous throughout the time period chosen for patch application.

It should also be noted that the present invention is directed to the administration of nitroglycerin to individuals in need of nitroglycerin therapy, generally, and thus encompasses transdermal methods and systems designed for a variety of indications, e.g., the relief and treatment of angina pectoris, congestive heart failure, and the like.

In another aspect of the invention, a therapeutic system is provided for administering nitroglycerin transdermally, at relatively high fluxes as noted above, in the form of a skin patch. The skin patch is a laminated composite containing an upper backing layer that is substantially impermeable to the drug, and at least one drug/enhancer reservoir, one of which forms the basal surface of the device and is designed to adhere to the skin during use. The reservoir contains both the nitroglycerin and a permeation enhancer selected from the group consisting of sorbitan esters and aliphatic alcohols as described above.

In still another aspect of the invention, such a laminated composite is provided which further includes a strippable protective release liner laminated to the basal surface of the drug reservoir. The release liner is a disposable element designed to protect the exposed reservoir surface prior to use. The release liner, for ease of removal, is preferably a two-part structure in which a first strippable protective sheet partially overlaps a second strippable protective sheet, giving rise to a tab extending from the basal surface of the patch.

DETAILED DESCRIPTION OF THE INVENTION

Figure 1:
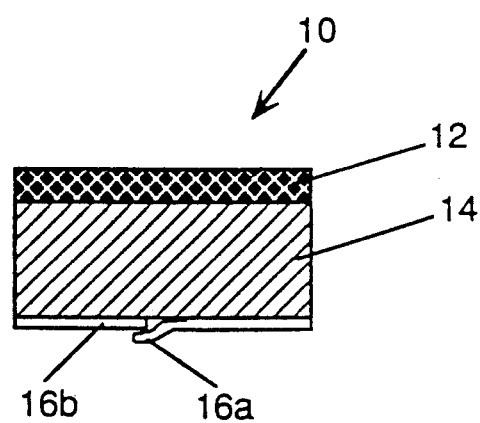
FIG. 1 is a schematic sectional view through a laminated transdermal system of the invention.

In describing and claiming the present invention, the following terminology will be used in accordance with the definitions set out below.

"Nitroglycerin" shall mean 1,2,3-propanetriol trinitrate, i.e., the compound having the structural formula

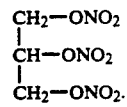

"Penetration enhancement" or "permeation enhancement" as used herein relates to an increase in the permeability of skin to nitroglycerin, i.e., so as to increase the rate at which nitroglycerin permeates into and through the skin. A "permeation enhancer" is a material which achieves permeation enhancement of nitroglycerin, and a "penetration enhancing amount" of an enhancer as used herein means an amount effective to enhance skin penetration of nitroglycerin to a desired degree.

"Transdermal" shall mean passage of a drug through the skin or mucosal tissue and into the bloodstream to achieve effective therapeutic blood levels of the drug.

"Carriers" or "vehicles" as used herein refer to carrier materials without pharmacological activity which are suitable for administration in conjunction with the presently disclosed and claimed compositions, and include any such carrier or vehicle materials known in the art, e.g., any liquid, gel, solvent, liquid diluent, solubilizer, or the like. The carriers and vehicles suitable herein are "pharmaceutically acceptable" in that they are nontoxic, do not interfere with drug delivery, and are not for any other reasons biologically or otherwise undesirable. Examples of specific suitable carriers and vehicles for use herein include water, mineral oil, silicone, inorganic gels, aqueous emulsions, liquid sugars, waxes, petroleum jelly, and a variety of other oils and polymeric materials.

By a "therapeutically effective" amount of nitroglycerin is meant a nontoxic but sufficient amount of nitroglycerin to provide the desired therapeutic effect.

The invention is thus in one embodiment a method for administering nitroglycerin transdermally so as to achieve relatively high transdermal fluxes, wherein the method involves administering, through a predetermined area of intact skin, and for a predetermined period of time, nitroglycerin, and a permeation enhancer selected from the group consisting of sorbitan esters, aliphatic alcohols R-OH where R is as defined below, and mixtures thereof. The sorbitan esters which are useful in conjunction with the present invention have the structure

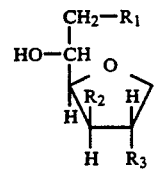

wherein the substituent $R_1$ has the structure —O(CO)R', where R' is selected from the group consisting of saturated, mono-unsaturated, di-unsaturated and tri-unsaturated aliphatic hydrocarbon substituents of 7 to 21 carbon atoms and may be substituted with 1 to 3 hydroxyl groups. The substituents R2 and R3 may be the same or different and are selected from the group consisting of hydroxyl and —O(CO)R' as defined above. $R_1$, $R_2$ and $R_3$, may be, for example, lauryl, myristyl, palmityl, stearyl, palmitoleyl, oleyl, linoleyl, linolenyl, or ricinoleyl esters, or the like. Exemplary sorbitan esters are sorbitan monoester $R_1$ is as defined above, and $R_2$ and $R_3$ are both hydroxyl. Particularly preferred compounds within the class of sorbitan monoesters are sorbitan monooleate and sorbitan monolaurate. As noted above, the nitroglycerin may be administered either with such a sorbitan ester or with an aliphatic alcohol R—OH, or with both types of compounds in a single permeation enhancer composition. If an alcohol is used, it is a $C_8$-$C_{22}$ aliphatic alcohol with "R" of the formula R-OH defined as a saturated, mono-unsaturated, di-unsaturated or tri-unsaturated $C_8$-$C_{22}$ aliphatic hydrocarbon substituent, and may be substituted with one to three additional hydroxyl groups. Preferred alcohols for use herein are oleyl and lauryl alcohols, with oleyl alcohol particularly preferred.

The nitroglycerin and the selected permeation enhancer or enhancers are preferably administered to the individual simultaneously, in a single composition. The amounts of the drug and enhancer in the composition may vary, depending on the system used for administration, e.g., ointment, gel, transdermal patch, or the like. The quantities of the two components will also depend on the desired dosage, the indication addressed, the medical history of the patient, etc. A preferred mode of administration, however, is via a transdermal patch, wherein the preferred quantities of the various components will be outlined below.

In a preferred embodiment, the nitroglycerin and the selected permeation enhancer or enhancers are administered such that flux is increased by at least about 50% relative to that which would be achieved in the absence of a permeation enhancer, that is, typically, a flux on the order of at least about 10 $\mu g/cm^2/hr$, preferably at least about 20 $\mu g/cm^2/hr$, most preferably at least about 30 $\mu g/cm^2/hr$, is achieved. It will be appreciated by those skilled in the art of transdermal drug delivery that the foregoing numbers are approximate, as transdermal flux may vary with the individual undergoing treatment as well as the particular skin site chosen for transdermal drug delivery.

It is also preferred that the time period for administration be on the order of 12 to 36 hours, optimally about 12 to 24 hours, during which time drug delivery is substantially continuous.

Preferred daily dosages obtained with the present methods and systems are typically in the range of 2.5 to 50 mg, more typically in the range of about 2.5 to 20 mg. The targeted daily dosage will depend on the individual being treated, the indication addressed, the length of time the individual has been on the drug, and the like. Generally, and as noted above, the present methods and systems enable transdermal administration of nitroglycerin at somewhat higher transdermal fluxes than enabled with the majority of previously known transdermal nitroglycerin systems, and may thus be useful for treating disorders which require a higher daily dosage than is typical (e.g., congestive heart failure), or for treating patients who have developed some tolerance for the drug. The invention also enables the use of conveniently sized small patches.

Transdermal delivery of nitroglycerin with the permeation enhancers of the invention enable the use of a skin area for drug administration in the range of approximately 1.0 $cm^2$ to about 100 $cm^2$. At higher transdermal fluxes, smaller skin areas within the aforementioned range may be targeted, i.e., less than about 25 $cm^2$ or, more preferably, less than about 10 $cm^2$.

A transdermal delivery system for the administration of nitroglycerin can be constructed with the drug/enhancer composition described hereinabove. Preferred transdermal drug delivery systems for use herein are laminated composites which contain one or more drug/permeation enhancer reservoirs, a backing layer and, optionally, one or more additional layers (e.g., additional drug and/or enhancer reservoirs) as those skilled in the art of transdermal drug delivery will readily appreciate. FIG. 1 depicts an exemplary system, generally designated 10, that when applied to skin administers nitroglycerin as outlined above. System 10 is a laminated composite in which the top layer 12 is a backing layer, its face forming the top surface of the composite. The drug reservoir, containing nitroglycerin, enhancer(s) as described herein, and optional carriers or vehicles, is shown at 14, immediately below and adjacent to the backing layer. Prior to use, the laminate also includes a strippable protective release liner shown as containing two sheets 16a and 16b, the first sheet 16a partially overlapping the second sheet 16b as will be described below. Additional structural layers and/or additional drug/enhancer reservoirs may also be present.

The drug reservoir is preferably comprised of a contact adhesive which is a pressure-sensitive adhesive suitable for long-term skin contact. It must also be physically and chemically compatible with nitroglycerin, the enhancers employed, and any carriers or vehicles incorporated into the drug/enhancer composition. Further, the adhesive selected for use as the reservoir layer must be such that the nitroglycerin is at least somewhat soluble in the adhesive. The drug reservoir will generally be in the range of about 2 to 4 mils in thickness. Suitable adhesives for use as the drug reservoir include polysiloxanes, polyacrylates, polyurethanes, tacky rubbers such as polyisobutylene, and the like. Particularly preferred contact adhesives for use as the drug reservoir herein are cross-linked acrylates (e.g., "Durotak ® 80-1194," available from National Starch & Chemical Co. or "Gelva ® 737" available from Monsanto).

The backing layer, which is, as shown, adhered to the drug reservoir and serves as the upper layer of the device during use, functions as the primary structural element of the device. The backing layer is made of a sheet or film of a preferably flexible elastomeric material that is substantially impermeable to nitroglycerin. The layer will typically be on the order of 1.0 to about 4.0 mils in thickness, and is preferably of a material that permits the device to follow the contours of the skin, such that it may be worn comfortably on any skin area, e.g., at joints or other points of flexure. In this way, in response to normal mechanical strain, there is little or no likelihood of the device disengaging from the skin due to differences in the flexibility or resiliency of the skin and the device. Examples of polymers useful for the backing layer herein are polyetheramide block polymers such as PEBAX polymers, polyethylenemethyl methacrylate block polymers (EMA) such as NUKRELL polymers, polyester block copolymers such as HYTREL polymers, polyethylene, polypropylene, polyesters, polyethylene vinyl acetate, polyvinylidene chloride, and the like. The backing layer may also comprise laminates of one or more of the foregoing polymers. The presently preferred backing material is polyethylene.

The release liner is a disposable element which serves only to protect the device prior to application. Typically, the release liner is formed from a material impermeable to the drug, vehicle, and adhesive, and which is easily stripped from the contact adhesive that serves as the drug reservoir layer. Preferred release liners for use herein are those which are generally suitable for use in conjunction with pressure-sensitive adhesives. Silanized polyester films are presently preferred.

In a preferred embodiment, as noted above, a two-part release liner is used, wherein a first strippable protective sheet (shown as 16a in the Figure) partially overlaps a second strippable protective sheet 16b) such that the of the overlap gives rise to which extends from the basal surface of the laminate, enabling ready removal of the strippable sheets from the reservoir layer.

The preferred laminated composites of the invention are as shown in FIG. 1, having a backing layer, a drug reservoir, and a two-piece release liner; the drug reservoir preferably contains approximately 30 wt. % to 45 wt. %, more preferably 37.5 wt. % nitroglycerin, 2.5 wt. % to 20 wt. %, more preferably 5.0 wt % to 15 wt. % enhancer, which may be either a sorbitan ester as defined elsewhere herein, a $C_8$-$C_{22}$ aliphatic alcohol R-OH, or a mixture thereof, with the remainder of the drug reservoir comprised of adhesive. In a patch size of about 2.5 to 100 $cm^2$, the aforementioned relative quantities of the various components give rise to the desired transdermal flux and drug dosage described above, substantially continuously over an approximately 12 hr to 24 hr period. To use these laminated composites, one is applied directly to the skin of a mammalian patient, to release the nitroglycerin/enhancer composition to the skin, allowing nitroglycerin to permeate into the circulation. The adhesive layer which serves as the drug reservoir should be in firm contact with the skin.

In general, devices of the invention are fabricated using methods standard in the art, e.g., solvent-evaporation film casting in which all components of the drug/enhancer composition are admixed with the adhesive which will serve as the drug reservoir, and cast onto a substrate which is either the backing layer or release liner. Other layers are then laminated to this initial structure.

It is to be understood that while the invention has been described in conjunction with the preferred specific embodiments thereof, the foregoing description as well as the examples which follow are intended to illustrate and not limit the scope of the invention.

EXAMPLE 1

Nitroglycerin in ethanol (10 vol. %) was obtained from ICI Americas, Inc., Delaware; polyacrylate adhesive solution (Durotak ® 80-1194) was obtained from National Starch & Chemical Co., N.J. Oleyl alcohol was obtained from Henkel Corp., La Grange, Ill. (HD Eutaonl, ultra pure grade). The polyacrylate adhesive solution, nitroglycerin solution and oleyl alcohol were mixed in the required proportion to provide a final solution which upon solvent evaporation would contain 37.5 wt. % nitroglycerin, 5 wt. % oleyl alcohol and 57.5 wt. % polyacrylate adhesive. This solution was roto-evaporated to increase its viscosity to facilitate casting as a film. The concentrated solution was cast onto the silanized surface of a polyester release liner (Release Technologies, 2-EST-A-S242M), using a 10 mil gap Gardner knife. The cast adhesive was then dried at 80° C for 15 minutes in a convection oven to yield a final 0.0025 inch thick adhesive coating A 0.0025 inch thick low density polyethylene film (Schoeller Technical Paper Co., New York) was then laminated onto the dried adhesive surface to produce a three-layer transdermal matrix system construction. Following the same procedure outlined above, another transdermal matrix system with the final composition of 35 wt. % nitroglycerin and 65 wt. % polyacrylate adhesive was prepared. This matrix did not contain any enhancer.

The in vitro skin flux of nitroglycerin across human cadaver skin was evaluated as described by Merrit and Cooper (J. Controlled Release (1984)1:161) using a high-performance liquid chromatography (HPLC) method for nitroglycerin assay as described in Table I. For these studies the release liner was removed from a previously cut section of the above transdermal matrix construction. The adhesive matrix was then positioned onto the stratum corneum surface of heat separated human epidermis and the skin, with the adhering transdermal system, was then immediately mounted onto the diffusion cell. The steady state flux ($\mu g/cm^2/hr$) of nitroglycerin was determined by linear regression analysis of the cumulative amount of nitroglycerin permeating ($\mu g/cm^2$) across the skin as a function of the time (hr). As controls, the flux of nitroglycerin from an unenhanced nitroglycerin patch (NitroDur II, Key Pharmaceuticals) and an enhanced nitroglycerin patch (Minitran ®, Riker Pharmaceuticals) were evaluated in parallel.

TABLE I

| HPLC Assay Method for Nitroglycerin | |
|---|---|
| Mobile Phase: | 50% (vol.) acetonitrile 50% (vol.) water |
| Flow Rate: | 1.3 ml/minute |
| Column: | Partisphere $C_{18}$ (Whatman) |
| Injection Volume: | 20 $\mu l$ |
| Wave Length: | 210 nm |
| Retention Time: | 3.0 minutes |
| Run Time: | 5.0 minutes |

Table II provides the skin flux in two different experiments obtained from the controls and the transdermal matrix patches prepared according to the method described above. The flux obtained from the oleyl alcohol matrix is much higher than that from the unenhanced NitroDur II control patch and the unenhanced nitroglycerin patch prepared as described above. Furthermore, the oleyl alcohol matrix produced significantly higher nitroglycerin skin flux than the enhanced control patch, Minitran.

TABLE II

| | Nitroglycerin Skin Flux ($\mu g/cm^2/hr$)[a] | |
|---|---|---|
| Formulation | Skin 1 | Skin 2 |
| NitroDur II | 20.58 ± 2.60 | 29.92 ± 4.02 |
| Minitran | 26.63 ± 5.92 | 36.69 ± 2.91 |
| 65/35[b] | 24.21 ± 2.84 | 30.68 ± 2.80 |
| 57.5/37.5/5[c] | 38.56 ± 0.96 | 45.63 ± 4.33 |

[a] N = 4, mean ± standard deviation
[b] weight percent of adhesive/nitroglycerin (no enhancer)
[c] weight percent of adhesive/nitroglycerin/oleyl alcohol

EXAMPLE 2

Nitroglycerin was premixed into the National Starch Durotak ® 80-1194 polyacrylate adhesive by Atlas Powder Company to provide a final solution containing 22.1 wt. % nitroglycerin, 35.8 wt. % solid acrylic adhesive and, 42.1 wt. % total solvents. Oleyl alcohol (Henkel) or sorbitan monooleate ("Arlacel ® 80"; ICI Americas) was then dissolved into the nitroglycerin-/adhesive solution at various levels to provide final matrix compositions ranging from 0 to 7.5 wt. % enhancer upon drying. These solutions were then cast onto silanized release liners, dried at 80° C. for 15 minutes, and finally laminated onto the polyethylene backing film as described in Example 1. Transdermal nitroglycerin delivery was then determined as a function of enhancer loading as described in Example I using the Minitran Patch (Riker Labs) as a control. Results are presented in Table III.

TABLE III

| Formulation | Nitroglycerin Skin Flux ($\mu g/cm^2/hr$)[a] | |
|---|---|---|
| | Oleyl Alcohol | Arlacel 80 |
| 60.0/37.5/2.5[b] | 39.61 ± 1.94 | 39.18 ± 4.28 |
| 58.75/36.25/5.0[b] | 41.27 ± 4.65 | 42.63 ± 7.55 |
| 57.25/35.25/7.5[b] | 47.02 ± 2.63 | 36.04 ± 8.13 |
| Minitran Control | 31.52 ± 1.79 | 31.52 ± 1.79 |

[a]N = 4
[b]weight percent ratios of adhesive/nitroglycerin/enhancer

In general, nitroglycerin flux was found to increase with increasing enhancer (either oleyl alcohol or Arlacel 80) content. Further, higher nitroglycerin flux values were observed with all enhancer loadings in the experimental matrix compositions than with the Minitran control.

EXAMPLE 3

The procedure of Example 1 is repeated using lauryl alcohol in place of oleyl alcohol. Increased transdermal flux relative to an unenhanced nitroglycerin patch is also obtained.

EXAMPLE 4

The procedure of Example 1 is repeated but palmityl alcohol is used in place of oleyl alcohol As in the preceding examples, enhanced transdermal flux relative to an unenhanced nitroglycerin patch is obtained.

EXAMPLE 5

The procedure of Example 1 is repeated but linoleyl alcohol is used in place of oleyl alcohol. As in the preceding examples, enhanced transdermal flux relative to an unenhanced nitroglycerin patch is obtained.

EXAMPLE 6

The procedure of Example 2 is repeated using lauryl alcohol in place of oleyl alcohol. Increased transdermal flux relative to an unenhanced nitroglycerin patch in also obtained.

EXAMPLE 7

The procedure of Example 2 is repeated using palmityl alcohol in place of oleyl alcohol. Enhanced transdermal flux relative to that obtained from an unenhanced nitroglycerin patch is obtained.

EXAMPLE 8

The procedure of Example 2 is repeated using linoleyl alcohol in place of oleyl alcohol. Enhanced transdermal flux relative to that obtained from an unenhanced nitroglycerin patch is obtained.

EXAMPLE 9

The procedure of Example 2 is repeated using sorbitan monolaurate in place of sorbitan monooleate (e.g., "Arlacel ® 20" from ICI Americas). Enhanced transdermal flux relative to an unenhanced nitroglycerin system is obtained.

EXAMPLE 10

The procedure of Example 2 is repeated using sorbitan monopalmitate in place of sorbitan monooleate (e.g., "Arlacel ® 40" from ICI Americas). Enhanced transdermal flux relative to that obtained from with an unenhanced nitroglycerin system is obtained.

EXAMPLE 11

The procedure of Example 2 is repeated using sorbitan trioleate in place of sorbitan monooleate (e.g., "Arlacel ® 85" from ICI Americas). As with the preceding examples, the transdermal flux obtained is higher than that which would be obtained for an unenhanced nitroglycerin patch.

EXAMPLE 12

The enhanced transdermal delivery of nitroglycerin from acrylic matrices containing 5 wt. % enhancer (oleyl alcohol or Arlacel ® 80) was evaluated using 3 different donor skins. Enhanced nitroglycerin matrices were prepared as described in Example 2, nitroglycerin skin flux was determined as described in Example 1 using the NitroDur II and Minitran as controls. In vitro skin flux results are presented in Table IV.

TABLE IV

| Formulation | Nitroglycerin Skin Flux ($\mu g/cm^2/hr$) | | |
|---|---|---|---|
| | Skin 1 | Skin 2 | Skin 3 |
| NitroDur II | — | 26.06 ± 5.65 | 16.34 ± 4.64 |
| Minitran | 39.97 ± 3.69 | 44.14 ± 5.95 | 20.17 ± 1.61 |
| 5% Oleyl Alcohol[a] | 55.99 ± 4.80 | 50.57 ± 6.53 | 30.63 ± 5.04 |
| 5% Arlacel 80[a] | 57.45 ± 3.81 | 51.86 ± 10.72 | 26.57 ± 2.78 |

[a]58.7% wt acrylic adhesive, 36.3% wt nitroglycerin, 5.0% wt enhancer

The flux obtained from both oleyl alcohol and Arlacel 80 enhanced matrices was nearly double that obtained from the unenhanced NitroDur II control patch. Further, both enhanced matrix formulations produced consistently higher nitroglycerin skin flux than the enhanced control patch, Minitran.

EXAMPLE 13

An easy to open release tab can be prepared by overlapping two sections of the release liner by approximately ⅛ inch. The adhesive/drug/enhancer solution can then be past onto a first release liner, dried and laminated to the backing film as described in the above examples. The first release liner is then removed and the overlapping release liner is then laminated onto the adhesive surface in its place. Final transdermal patches are then die cut with the overlapping release liner section spatially within the final patch. Alternatively, the first release liner can be control depth slit following the lamination of the backing film. A section of the slit liner is then removed and a new section relaminated onto the exposed adhesive area such that the new liner section overlaps the remaining, slit prior liner which was not removed from the original laminate. Final patches are then die cut as previously described.

We claim:
1. A laminated composite for administering nitroglycerin transdermally through a predetermined area of skin over a sustained time period, comprising:

(a) a backing layer that is substantially impermeable to nitroglycerin,
(b) a reservoir layer comprising an adhesive polymer the basal surface of the reservoir layer being adapted to be adhered to the skin, and
(c) contained in the reservoir layer,
   (i) nitroglycerin, and
   (ii) a permeation enhancer consisting essentially of a sorbitan ester having the structural formula

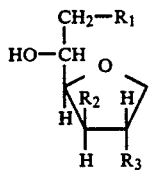

wherein $R_1$ has the structure —O(CO)R', where R' is selected from the group consisting of saturated, mono-unsaturated, di-unsaturated, or tri-unsaturated aliphatic hydrocarbon substituents of 7 to 21 carbon atoms optionally containing 1 to 3 hydroxyl groups, and $R_2$ and $R_3$ are selected from the group consisting of hydroxyl and —O(CO)R'; and
an alcohol R—OH, wherein R is a saturated or mono-unsaturated aliphatic hydrocarbon substituent of 8 to 22 carbon atoms and may be either unsubstituted or substituted with one to three additional hydroxyl groups,
wherein the nitroglycerin and the permeation enhancer are present in the reservoir in an amount sufficient to enable transdermal administration of the nitroglycerin at a flux of at least about 50% higher than that obtained in the absence of said enhancer.

2. The laminated composite of claim 1 wherein the sustained time period is about 12 to about 24 hours.

3. The laminated composite of claim 1 wherein the predetermined area of skin is less than about 25 cm².

4. The laminated composite of claim 1 wherein the predetermined area of skin is less than about 10 cm².

5. The laminated composite of claim 1 wherein the reservoir comprises a crosslinked acrylic adhesive.

6. The laminated composite of claim 1 wherein $R_2$ and $R_3$ are both hydroxyl.

7. The laminated composite of claim 6 wherein the enhancer is sorbitan monooleate or sorbitan monolaurate.

8. The laminated composite of claim 7 wherein the enhancer is sorbitan monooleate.

9. The laminated composite of claim 1 wherein the enhancer is oleyl alcohol.

10. The laminated composite of claim 1 wherein the enhancer is lauryl alcohol.

11. The laminated composite of claim 1 wherein the reservoir is about 2–4 mils in thickness.

12. The laminated composite of claim 1, further comprising a strippable protective release liner laminated to the basal surface of the reservoir.

13. The laminated composite of claim 12, wherein said release liner comprises a first strippable protective sheet partially overlapping a second strippable protective sheet, and wherein the area of overlap gives rise to an extending tab which enables ready removal of the first strippable sheet from the reservoir layer.

14. A laminated composite for the transdermal administration of nitroglycerin through a predetermined area of skin over a sustained time period, comprising;
(a) a backing layer that is substantially impermeable to nitroglycerin, and
(b) a reservoir layer, the basal surface of which is adapted to be adhered to the skin, comprising:
   (i) approximately 35 wt. % to 67.5 wt. % adhesive;
   (ii) approximately 30 wt. % to 45 wt. % nitroglycerin; and
   (iii) approximately 2.5 wt. % to 20 wt. % permeation enhancer consisting essentially of
a sorbitan ester having the structural formula

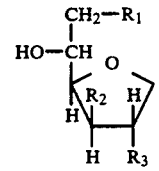

wherein $R_1$ has the structure —O(CO)R', where R' is selected from the group consisting of saturated, mono-unsaturated, di-unsaturated, or ti-unsaturated aliphatic hydrocarbon substituents of 7 to 21 carbon atoms optionally containing 1 to 3 hydroxyl groups, and $R_2$ and $R_3$ are selected from the group consisting of hydroxyl and —O(CO)R'; and
an alcohol R—OH, wherein R is a saturated or mono-unsaturated aliphatic hydrocarbon substituent of 8 to 22 carbon atoms and may be either unsubstituted or substituted with one to three additional hydroxyl groups.

* * * * *